United States Patent [19]

Comte et al.

[11] Patent Number: 5,130,313
[45] Date of Patent: Jul. 14, 1992

[54] SEROTONIN ANTAGONISTS, THEIR PREPARATION AND MEDICATIONS CONTAINING THEM

[75] Inventors: Marie-Thérèse Comte, Chevilly Larue; Claude Gueremy, Houilles; Jean-Luc Malleron, Marcoussis; Jean-Francois Peyronel, Palaiseau; Alain Truchon, Lyons, all of France

[73] Assignee: Rhone-Poulenc Sante, Antony, France

[21] Appl. No.: 627,101

[22] Filed: Dec. 13, 1990

[30] Foreign Application Priority Data

Dec. 13, 1989 [FR] France .................. 89 16459
Jun. 5, 1990 [FR] France .................. 90 06943

[51] Int. Cl.$^5$ .................. C07D 471/16; C07D 401/06; C07D 403/06; C07D 417/06
[52] U.S. Cl. .................. 514/253; 514/293; 544/9; 544/33; 544/360; 544/361; 544/368; 544/370; 544/372; 544/392; 546/83; 546/198; 546/199; 546/200; 546/201; 546/225; 546/232; 546/270; 546/271; 546/273; 546/329; 546/334
[58] Field of Search .................. 546/83; 544/361; 514/253, 293

[56] References Cited

U.S. PATENT DOCUMENTS

| | | | |
|---|---|---|---|
| 3,303,189 | 2/1967 | Loev .................. | 260/243 |
| 4,110,449 | 8/1978 | Wade et al. .................. | 540/368 |
| 4,330,542 | 5/1982 | Descamps et al. .................. | 544/401 |

FOREIGN PATENT DOCUMENTS 330065  8/1989  European Pat. Off. .

*Primary Examiner*—Mark L. Berch
*Attorney, Agent, or Firm*—Morgan & Finnegan

[57] ABSTRACT

This invention relates to compounds of formula:

$$R_2-N-(CH_2)_n-R_1 \atop R_3 \qquad (I)$$

in which
  $R_1$ denotes
    a 1,2,3,6-tetrahydro-1-pyridyl radical substituted in the 4-position by an optionally substituted phenyl, optionally substituted 3-indolyl or 3-(5-hydroxyindolyl) radical,
    a 1-piperazinyl radical substituted in the 4-position by an optionally substituted phenyl, 1,2-benzisothiazol-3-yl, 1,2-benzisoxazol-3-yl or 2-pyridyl radical,
    a piperidino radical substituted in the 4-position by an optionally substituted phenyl, bis(4-fluorophenyl)methylene, 4-fluorobenzoyl, optionally substituted 2-oxo-1-benzimidazolinyl, optionally substituted 3-indolyl or 3-(5-hydroxyindolyl) radical, by two phenyl radicals or a hydroxyl radical and an optionally substituted phenyl radical
  $R_2$ denotes a radical $SO_2R_4$ in which $R_4$ denotes an alkyl or phenyl radical,
  $R_3$ denotes a phenyl or naphthyl radical,
  or else $R_2$ and $R_3$ together with the nitrogen atom to which they are attached form a ring,
  n is equal to 2, 3 or 4, processes for their preparation and medications containing them.

The invention relates to treating a disease ameliorated by serotonin.

5 Claims, No Drawings

SEROTONIN ANTAGONISTS, THEIR PREPARATION AND MEDICATIONS CONTAINING THEM

DESCRIPTION OF THE INVENTION

The present invention relates to compounds of formula:

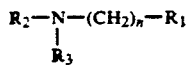  (I)

their salts, processes for their preparation and medications containing them.

In formula (I):

$R_1$ denotes a 1,2,3,6-tetrahydro-1-pyridyl radical substituted in the 4- position by (a) a phenyl radical, (b) a phenyl radical substituted by a halogen atom or an alkyl, hydroxyl or alkoxy radical, (c) a 3-indolyl radical, (d) a 3-indolyl radical substituted on the nitrogen atom by an alkyl or alkylcarbonyl radical and/or in the 5- position by a chlorine or fluorine atom or (e) a 3-(5-hydroxyindolyl) radical, a 1-piperazinyl radical substituted in the 4-position by (a) a phenyl radical, (b) a phenyl radical substituted by an alkoxy, alkyl, hydroxyl, nitro or amino radical or a halogen atom, (c) a 1,2-benzisothiazol-3-yl radical, (d) a 1,2-benzisoxazol-3-yl radical or (e) a 2-pyridyl radical, a piperidino radical substituted in the 4- position by (a) a phenyl radical, (b) a phenyl radical substituted by a halogen atom or a hydroxyl, alkyl or alkoxy radical, (c) two phenyl radicals, (d) a bis(4-fluorophenyl)methylene radical, (e) a 4-fluorobenzoyl radical, (f) a 2-oxo-1-benzimidazolinyl radical, (g) a 2-oxo-1-benzimidazolinyl radical substituted in the 3-position by an alkylcarbonyl or benzoyl radical, (h) a hydroxyl radical and a phenyl radical optionally substituted by an alkyl, alkoxy or hydroxyl radical or a halogen atom, (i) a 3-indolyl radical, (j) a 3-indolyl radical substituted on the nitrogen atom by an alkyl or alkylcarbonyl radical and/or in the 5-position by a chlorine or fluorine atom or (k) a 3-(5-hydroxyindolyl) radical, $R_2$ denotes a radical $SO_2R_4$ in which $R_4$ denotes an alkyl or phenyl radical, $R_3$ denotes a phenyl or naphthyl radical, or else $R_2$ and $R_3$ together with the nitrogen atom to which they are attached form a ring chosen from the formulae:

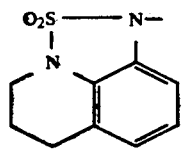

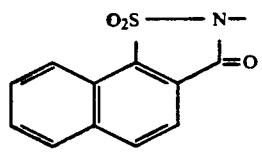

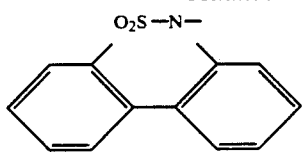

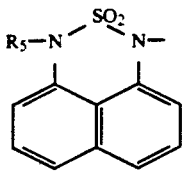

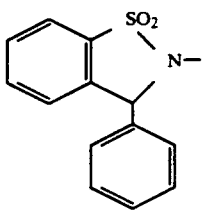

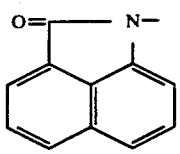

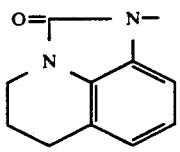

$R_5$ denotes an alkyl radical or a $-(CH_2)_n-R_1$ chain, n is equal to 2, 3 or 4.

In the definitions which precede and those which will be referred to below, the alkyl radicals contain from 1 to 4 carbon atoms as a straight or branched chain and the halogen atoms are preferably fluorine, chlorine or bromine atoms.

The invention also relates to the salts of the compounds of formula (I) with inorganic or organic acids.

The compounds of formula (I), with the exception of those in which R denotes a 4-aminophenyl-1-piperazinyl radical, can be prepared by the action of a derivative of formula:

  (II)

in which $R_2$ and $R_3$ have the same meanings as in formula (I) on a halogenated derivative of formula:

  (III)

in which Hal denotes a halogen atom and n has the same meanings as in formula (I) and $R^1$ has the same meanings as above.

This reaction is preferably carried out in the presence of a base such as an alkali metal hydride, an alkali metal hydroxide or an alkali metal carbonate, in an inert solvent such as dimethylformamide or tetrahydrofuran, at a temperature between 20° C. and the boiling temperature of the solvent.

The compounds of formula (II) can be prepared by applying or adapting methods described by H. P. Kaufmann et al., Ber., 6, 1499 (1922), F. Ullmann et al., Chem. Ber. 43, 2684 (1910) and C. W. Rees et al., J. Chem. Soc., 993 (1971) and methods described in the examples.

The halogenated derivatives of formula (III) can be obtained by the action of an amine of formula:

$$HR_1 \qquad (IV)$$

in which $R_1$ has the same meanings as in formula (III) on a dihalogenated derivative of formula:

$$Hal-(CH_2)_n-X \qquad (V)$$

in which Hal and X denote a halogen atom and n is equal to 2, 3 or 4.

This reaction is generally carried out in an inert solvent such as dimethylformamide or acetonitrile, in the presence of a base such as an alkali metal carbonate, at a temperature between 20° C. and the boiling temperature of the solvent.

The amines of formula (IV) are marketed or can be obtained by applying or adapting methods described by R. L. Duncan et al., J. Med. Chem., 13, 1 (1970), L. Nedelec et al., Eur. J. Med. Chem. 22, 33 (1987), D. K. Yunk et al., J. Med. Chem., 21, 1301 (1978), J. P. Yevich et al., J. Med. Chem., 29, 3, 359 (1986), L. Thunus et al., Ann. Pharm., 38, 353 (1980), L. Gootes et al., Arzneim Forsch, 17, 1145 (1967); J. Bergman et al., J. Het. Chem., 1071 (1970) and in patents DE 2,139,084, BE 62,630, EP 110,435, U.S. Pat. No. 4,470,989 and U.S. Pat. No. 3,575,990 and methods described in the examples.

The compounds of formula (I), with the exception of those in which $R_1$ denotes a 4-aminophenyl-1-piperazinyl radical, can also be obtained by the action of a derivative of formula:

$$R_2-N-(CH_2)_n-Hal \qquad (VI)$$
$$\phantom{R_2-N-}|$$
$$\phantom{R_2-N-}R_3$$

in which $R_2$, $R_3$ and n have the same meanings as in formula (I) and Hal denotes a halogen atom, on a derivative of formula (IV) in which $R_1$ has the same meanings as above.

This reaction is generally carried out in an inert solvent such as tetrahydrofuran or dimethylformamide, in the presence of a base such as an alkali metal bicarbonate or a triethylamine, at the boiling temperature of the reaction mixture.

The derivatives of formula (VI) can be obtained by the action of a derivative of formula (II) on a dihalogenated derivative of formula (V).

This reaction is carried out in an inert solvent such as dimethylformamide, by means of sodium hydride at a temperature between 20° C. and the boiling temperature of the solvent.

The compounds of formula (I) in which $R_1$ denotes a 4-aminophenyl-1-piperazinyl radical can be obtained by reduction of the corresponding compounds of formula (I) in which R denotes a 4-nitrophenyl-1-piperazinyl radical.

This reduction is generally carried out by means of stannous chloride and sodium borohydride in an alcohol such as methanol or ethanol, at a temperature between 20° and 70° C. or by means of iron and hydrochloric acid in water or a water-alcohol mixture, at a temperature between 20° C. and the reflux temperature of the reaction mixture.

The reaction mixtures obtained by the various processes described above are treated by conventional physical methods (evaporation, extraction, distillation, crystallization, chromatography, etc.) or chemical ones (salt formation, etc.).

The compounds of formula (I), in free base form, can be optionally converted into addition salts with an inorganic or organic acid by the action of such an acid in an organic solvent such as an alcohol, a ketone, an ether or a chlorinated solvent.

The compounds of formula (I) and their salts have advantageous properties. These compounds have serotonin antagonist (5 HT2 receptor) properties and are therefore useful for the treatment of disorders in which serotonin is involved, especially the disorders of the central nervous system, of the cardiovascular system and gastrointestinal disturbances.

In particular, these compounds are useful for the treatment of anxiety, of sleep disturbances, of depression, of psychoses and especially of schizophrenia, of migraine, of asthma, of hypertension and of urticaria, as analgesics and as inhibitors of platelet coagulation.

The affinity of the compounds of formula (I) for the central receptor sites containing serotonin (type S2) has been determined by a technique suggested by that of J. E. Leysen et al., Mol. Pharmacol., 21, 301 (1982), which consists in measuring the affinity of the products for the binding sites of tritiated ketanserine. In this test the $IC_5O$ of the compounds of formula (I) is generally lower than 25 nM.

The compounds of formula (I) exhibit a low toxicity. They are generally atoxic at 300 mg/kg by oral route in the mouse, as single administration.

Those of particular interest are the compounds in which $R_1$ denotes a 4-phenyl-1,2,3,6-tetrahydro-1-pyridyl, 4-phenylpiperidino, 4-(4-fluorobenzoyl)piperidino or 4-phenyl-1-piperazinyl radical, in which the phenyl nucleus is optionally substituted by a halogen atom or a hydroxyl radical.

The following compounds are of particular interest:

1-[3-(4-phenyl-1,2,3,6-tetrahydro-1-pyridyl)propyl]-5,6-dihydro(1H,4H)-1,2,5-thiadiazolo[4,3,2-ij]quinoline 2,2-dioxide 1-[3-(4-(4-fluorophenyl)piperazinyl)propyl]-5,6-dihydro(1H,4H)-1,2,5-thiadiazolo[4,3,2-ij]quinoline 2,2-dioxide 1-[3-(4-(4-hydroxyphenyl)piperazinyl)propyl]-5,6-dihydro(1H,4H)-1,2,5-thiadiazolo[4,3,2-ij]quinoline 2,2-dioxide (3RS)-2-[3-(4-(4-fluorophenyl)-1-piperazinyl)propyl]-3-phenyl-1,2-benzisothiazole 1,2-dioxide.

For therapeutic use, the compounds of formula (I) can be employed as they are or in the form of pharmaceutically acceptable salts.

As pharmaceutically acceptable salts there may be mentioned in particular the addition salts with inorganic acids such as hydrochlorides, sulphates, nitrates or phosphates or with organic ones, such as acetates, propionates, succinates, oxalates, benzoates, fumarates, maleates, methanesulphonates, isethionates, theophillineacetates, salicylates, phenolphthalinates, methylenebisx-oxynaphthoates or substituted derivatives of these derivatives.

EXAMPLES

The following examples, given without any limitation being implied, show how the invention can be put into practice.

EXAMPLE 1

A solution of 5,6-dihydro(1H,4H)-1,2,5-thiadiazolo[4,3,2-ij]quinoline 2,2-dioxide (2.6 g) in dry N,N-dimethylformamide (10 cc) is added dropwise to a suspension of sodium hydride (0.45 g, 80% suspension in oil) in N,N-dimethylformamide (20 cc). After 15 minutes, stirring, a solution of 1-(3-chloropropyl)-4-phenyl-1,2,3,6-tetrahydropyridine (3.51 g) in N,N-dimethylformamide (10 cc) is added. The reaction mixture is heated to 80° C. for 90 minutes and is then cooled and poured into a mixture of water (100 cc) and ethyl acetate (200 cc). The organic phase is washed with water, is dried over magnesium sulphate and is concentrated to dryness under reduced pressure (2.7 kPa). The residue is chromatographed on a column of silica gel (0.2-0.063-mm particle size, 4-cm diameter, 50-cm height) with ethyl acetate as eluent and with 125-cc fractions being collected. Fractions 2 to 6 are combined and concentrated to dryness under reduced pressure (2.7 kPa). After recrystallization from ethyl acetate, 1-[3-(4-phenyl-1,2,3,6-tetrahydro-1-pyridyl)propyl]-5,6-dihydro(1H,4H)-1,2,5-thiadiazolo[4,3,2-ij]quinoline 2,2-dioxide (3.7 g) is obtained, melting at 120° C.

5,6-Dihydro(1H,4H)-1,2,5-thiadiazolo[4,3,2-ij]quinoline 2,2-dioxide can be prepared as follows: sulphamide (6 g) is added to a solution of 8-amino-1,2,5,6-tetrahydroquinoline (9 g) in diglyme (90 cc) and the solution is heated to 160° C. for 90 minutes. The reaction mixture is cooled and then diluted in a mixture of water (300 cc) and ethyl acetate (300 cc). The organic phase is washed with water (3×300 cc), is dried over magnesium sulphate and is concentrated to dryness under reduced pressure (2.7 kPa). The residue is chromatographed on a column of silica gel (0.2-0.063-mm particle size, 6-cm diameter, 60-cm height), and eluted at a pressure of 0.7 bars of nitrogen with a mixture of cyclohexane and ethyl acetate (80-20 by volume), 125-cc fractions being collected. Fractions 12 to 22 are combined and concentrated to dryness under reduced pressure (2.7 kPa) to give 5,6-dihydro(1H,4H)-1,2,5-thiadiazolo[4,3,2-ij]quinoline 2,2-dioxide (9.4 g) melting at 96° C.

8-Amino-1,2,5,6-tetrahydroquinoline can be prepared according to the method described by Hazlewood et al., J. Pr. Soc., N. S. Wales, 71, 462 (1937-1938).

1-(3-Chloropropyl)-4-phenyl-1,2,4,6-tetrahydropyridine can be prepared as follows: a solution of 1-bromo-3-chloropropane (6 cc) and 4-phenyl-1,2,3,6-tetrahydropyridine (5.1 g) in acetonitrile (60 cc) is stirred at 25° C. for 20 hours with potassium carbonate (97 g). The mixture is filtered and then concentrated to dryness under reduced pressure (2.7 kPa). The residue is chromatographed on a column of silica gel (0.2-0.063-mm particle size, 4-cm diameter, 40-cm height) and eluted with a mixture of cyclohexane and ethyl acetate (50—50 by volume), 250-cc fractions being collected. Fractions 7 to 13 are combined and concentrated to dryness under reduced pressure (2.7 kPa) to give 1-(3-chloropropyl)-4-phenyl-1,2,3,6-tetrahydropyridine (5 g) in the form of a yellow oil.

Proton NMR (CDCl₃):

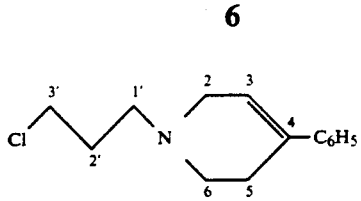

δ7.35 bd 2H ortho C₆H₅
δ7.28 bt 2H meta C₆H₅
δ7.18 bt 1H para C₆H₅
δ6 bs 1H ethyl CH (H₃)
δ3,6 t 2H CH₂Cl (2xH₃')
δ3.1 bs 2H CH₂-N (2xH₁')
δ2.7 t 2H C₂-N (2xH₁·)
δ2.55 m 4H CH₂ (2xH₆+2H₅)
δ2 m 2H CH₂ (2xH₂·)

EXAMPLE 2

A solution of 5,6-dihydro(1H,4H)-1,2,5-thiadiazolo[4,3,2-ij]quinoline 2,2-dioxide (5.34 g) in dry N,N-dimethylformamide (50 cc) is added dropwise to a suspension of sodium hydride (0.72 g, 80% suspension in oil) in N,N-dimethylformamide (20 cc). After 15 minutes' stirring, 1-(3-chloropropyl)-4-(4-fluorophenyl)piperazine (7.68 g) is added. The reaction mixture is heated to 100° C. for 1 hour and 30 minutes and is then cooled and poured into a mixture of water (300 cc) and ethyl acetate (500 cm). The organic phase is washed with water (3×200 cc), is dried over magnesium sulphate and is concentrated to dryness under reduced pressure (2.7 kPa). The residue is chromatographed on a column of silica gel (0.2-0.063-mm particle size, 6-cm diameter, 50-cm height) and eluted at a pressure of 0.7 bars of nitrogen with a mixture of cyclohexane and ethyl acetate (80-20 by volume), 125-cc fractions being collected. Fractions 10 to 28 are combined and concentrated to dryness under reduced pressure (2.7 kPa). The solid obtained is recrystallized from ethanol (80 cc). 1-[3-(4-(4-Fluorophenyl)piperazinyl)propyl]-5,6-dihydro(1H,4H)-1,2,5-thiadiazolo[4,3,2-ij]quinoline 2,2-dioxide (7.2 g) is obtained, melting at 98° C.

1-(3-Chloropropyl)-4-(4-fluorophenyl)piperazine can be obtained as follows: a solution of 1-bromo-3-chloropropane (68 cc) and 4-(4-fluorophenyl)piperazine (50 g) in acetonitrile (400 cc) is stirred at 25° C. for 20 hours with potassium carbonate (97 g). The mixture is filtered and then concentrated to dryness under reduced pressure (2.7 kPa). The residue is chromatographed on a column of silica gel (0.2-0.063-mm particle size, 9-cm diameter, 60-cm height) and eluted with ethyl acetate, 500-cc fractions being collected. Fractions 5 to 7 are combined and concentrated to dryness under reduced pressure (2.7 kPa) to give 1-(3-chloropropyl)-4-(4-fluorophenyl)piperazine (44.4 g) in the form of a yellow oil.

Proton NMR (CDCl₃):

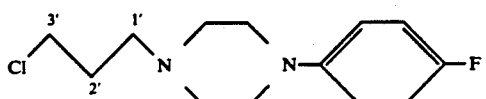

δ6.8 to 6.95 m 4H aromatics
δ3.6 t 2H CH₂Cl (2xH₃')
δ3.1 m 4H 2CH₂-N

δ2.6 m 4H 2CH$_2$-N
δ2,5 t 2H CH$_2$N (2xH$_{1'}$)
δ2 m 2H CH$_2$ (2xH$_{2'}$)

EXAMPLE 3

A solution of 1-(3-chloropropyl)-5,6-dihydro-(1H,4H)-1,2,5-thiadiazolo[4,3,2-ij]quinoline 2,2-dioxide (4 g), 4-(4-hydroxyphenyl)piperazine (4.75 g) and triethylamine (5.88 cc) in dry N,N-dimethylformamide (50 cc) is heated to reflux for 90 minutes and is then cooled and poured into a mixture of water (300 cc) and ethyl acetate (300 cc). The organic phase is washed with water (3×200 cc), is dried over magnesium sulphate and is concentrated to dryness under reduced pressure (2.7 kPa). The solid is recrystallized from ethyl acetate (300 cc) and dried. 1-[3-(4-(4-Hydroxyphenyl)-1-piperazinyl)propyl]-5,6-dihydro(1H,4H)-1,2,5-thiadiazolo[4,3,2-ij]quinoline 2,2-dioxide (2.8 g) is obtained, melting at 182° C.

1-(3-Chloropropyl)-5,6-dihydro(1H,4H)-1,2,5-thiadiazolo[4,3,2-ij]quinoline 2,2-dioxide can be obtained as follows: a solution of 5,6-dihydro-(1H,4H)-1,2,5-thiadiazolo[4,3,2-ij]quinoline 2,2-dioxide (4 g) in dry N,N-dimethylformamide (30 cc) is added dropwise to a suspension of sodium hydride (0.69 g, 80% suspension in oil) in N,N-dimethylformamide (20 cc). After 30 minutes' stirring, a solution of 1-bromo-3-chloropropane (3.25 g) in N,N-dimethylformamdide (20 cc) is added. The reaction mixture is stirred at 25° C. for 2 hours and is then diluted in a mixture of water (300 cc) and ethyl acetate (300 cc). The organic phase is washed with water (3×200 cc), is dried over magnesium sulphate and is concentrated to dryness under reduced pressure (2.7 kPa). The residue is chromatographed on a column of silica gel (0.2-0.063-mm particle size, 4-cm diameter, 50-cm height), and eluted at a pressure of 0.7 bars of nitrogen with a mixture of cyclohexane and ethyl acetate (80-20 by volume), 125-cc fractions being collected. Fractions 4 to 12 are combined and concentrated to dryness under reduced pressure (2.7 kPa) to give 1-(3-chloropropyl)-5,6-dihydro-(1H,4H)-1,2,5-thiadiazolo[4,3,2-ij]quinoline 2,2-dioxide (4.2 g) in the form of a yellow oil.

Proton NMR (CDCl$_3$):

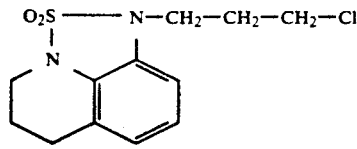

δ6.95 t 1H )
δ6.8 bd 1H ) 3 aromatics
δ6.73 bd 1H )
δ3.95 t 2H CH$_2$- N - SO$_2$
δ3.75 m 4H CH$_2$Cl and CH$_2$-N-SO$_2$
δ2.80 t 2H CH$_2$-<
δ2.35 and 2.20 2xm, 2xCH$_2$ (central CH$_2$)

1-(4-Hydroxyphenyl)piperazine dihydrobromide can be prepared as follows: an aqueous solution of hydrobromic acid (720 cc, 47%) is added over 30 minutes and at a temperature close to 20° C., to 4-(4-methoxyphenyl)piperazine dihydrochloride (70 g). The mixture is heated to boiling for 4 hours and then cooled to a temperature close to 20° C. Stirring is continued at this temperature for 15 hours and the mixture is then concentrated at 40° C. under reduced pressure (20 mm Hg; 2.7 kPa). The residual oil is taken up with acetonitrile (300 cc). The precipitate is separated off by filtration, washed with acetonitrile (2×50 cc) and diisopropyl ether (2×100 cc). 4-(4-Hydroxyphenyl)piperazine dihydrobromide (85.2 g) is obtained (melting point above 260° C.) and is employed in the crude state in the subsequent syntheses.

EXAMPLE 4

A solution of 1-(2-chloroethyl)-5,6-dihydro-(1H,4H)-1,2,5-thiadiazolo[4,3,2-ij]quinoline 2,2-dioxide (3.4 g), 4-(4-fluorophenyl)piperazine (2.25 g) and triethylamine (1.75 cc) in dry N,N-dimethylformamide (50 cc) is heated to reflux for 3 hours and is then cooled and poured into a mixture of water (300 cc) and ethyl acetate (300 cc). The organic phase is washed with water (3×200 cc), is dried over magnesium sulphate and is concentrated to dryness under reduced pressure (2.7 kPa). The residue is chromatographed on a column of silica gel (0.2-0.063-mm particle size, 4-cm diameter, 50-cm height) and eluted at a pressure of 0.7 bars of nitrogen with a mixture of cyclohexane and ethyl acetate (80-20 by volume), 125-cc fractions being collected. Fractions 33 to 43 are combined and concentrated to dryness under reduced pressure (2.7 kPa). After recrystallization from isopropyl ether (50 cc), 1-[2-(4-(4-fluorophenyl)-1-piperazinyl)ethyl]-5,6-dihydro(1H,4H)-1,2,5-thiadiazolo[4,3,2-ij]quinoline 2,2-dioxide (0.85 g) is obtained, melting at 118° C.

1-(2-Chloroethyl)-5,6-dihydro(1H,4H)-1,2,5-thiadiazolo[4,3,2-ij]quinoline 2,2-dioxide can be prepared as follows: a solution of 5,6-dihydro-(1H,4H)-1,2,5-thiadiazolo[4,3,2-ij]quinoline 2,2-dioxide (4 g) in dry N,N-dimethylformamide (20 cc) is added dropwise to a suspension of sodium hydride (0.69 g, 80% suspension in oil) in N,N-dimethylformamide (20 cc). After 15 minutes' stirring, a solution of 1-bromo-2-chloroethane (3.29g) in N,N-dimethylformamide (10cc) is added. The reaction mixture is stirred at 20° C. for 3 hours and then diluted in a mixture of water (300 cc) and ethyl acetate (300 cc). The organic phase is washed with water (3×200 cc), is dried over magnesium sulphate and is concentrated to dryness under reduced pressure (2.7 kPa). The residue is chromatographed on a column of silica gel (0.2-0.063-mm particle size, 4-cm diameter, 40-cm height) and eluted at a pressure of 0.7 bars of nitrogen with a mixture of cyclohexane and ethyl acetate (80-20 by volume), 125-cc fractions being collected. Fractions 8 to 16 are combined and concentrated to dryness under reduced pressure (2.7 kPa) to give 1-(2-chloroethyl)-5,6-dihydro(1H,4H)-1,2,5-thiadiazolo[4,3,2-ij]quinoline 2,2-dioxide (3.4 g) melting at 70° C.

EXAMPLE 5

The operation is as in Example 3, starting with 1-(3-chloropropyl)-5,6-dihydro(1H,4H)-1,2,5-thiadiazolo[4,3,2-ij]quinoline 2,2-dioxide (3.8 g), 4-(5-fluoro-3-indolyl)-1,2,3,6-tetrahydropyridine (2.9 g) and sodium bicarbonate (3.3 g) in a mixture of dimethylformamide (40 cc) and tetrahydrofuran (25 cc). The mixture is heated to boiling for 48 hours and is then cooled to a temperature close to 20° C. After purification by flash chromatography on a silica column, under a stream of argon at moderate pressure (0.5-1.5 bars) with ethyl acetate as eluent and recrystallization from boiling acetonitrile (200 cc), 1-[3-(4-(5-fluoro-3- indolyl)-1,2,3,6-tetrahydro-1-pyridyl)propyl]-5,6-dihydro(1H,4H)-1,2,5-thiadiazolo[4,3,2-ij]quinoline 2,2-dioxide (2.5 g) is obtained, melting at 178° C.

4-(5-Fluoro-3-indolyl)-1,2,3,6-tetrahydropyridine can be prepared according to the method described by L. Nedelec et al., Eur. J. Med. Chem., 22, 33 (1987).

EXAMPLE 6

A solution of 1-(4-chlorobutyl)-5,6-dihydro-(1H,4H)-1,2,5-thiadiazolo[4,3,2-ij]quinoline 2,2-dioxide (4.5 g), 4-(4-fluorophenyl)piperazine (2.7 g) and triethylamine (2.1 cc) in dry N,N-dimethylformamide (45 cc) is heated to reflux for 90 minutes and is then cooled and poured into a mixture of water (300 cc) and ethyl acetate (300 cc). The organic phase is washed with water (3×200 cc), is dried over magnesium sulphate and is concentrated to dryness under reduced pressure (2.7 kPa). The residue is chromatographed on a column of silica gel (0.2-0.063-mm particle size, 4-cm diameter, 50-cm height) and eluted at a pressure of 0.7 bars of nitrogen with a mixture of cyclohexane and ethyl acetate (30–70 by volume), 125-cc fractions being collected. Fractions 7 to 16 are combined and are concentrated to dryness under reduced pressure (2.7 kPa). After recrystallization from isopropyl ether (40 cc) 1-[4-(4-(4-fluorophenyl)-1-piperazinyl)butyl]-5,6-dihydro(1H,4H)-1,2,5-thiadiazolo-[4,3,2-ij]quinoline 2,2-dioxide (2.7 g) is obtained, melting at 87° C.

1-(4-Chlorobutyl)-5,6-dihydro(1H,4H)-1,2,5-thiadiazolo[4,3,2-ij]quinoline can be prepared as follows: a solution of 5,6-dihydro(1H,4H)-1,2,5-thiadiazolo[4,3,2-ij]quinoline 2,2-dioxide (4 g) in dry N,N-dimethylformamide (20 cc) is added dropwise to a suspension of sodium hydride (0.69 g, 80% suspension in oil) in N,N-dimethylformamide (20 cc). After 30 minutes' stirring, a solution of 1-bromo-4-chlorobutane (3.93 g) in N,N-dimethylformamide (20 cc) is added. The reaction mixture is stirred at 20° C. for 2 hours and then diluted in a mixture of water (200 cc) and ethyl acetate (200 cc). The organic phase is washed with water (3×200 cc), is dried over magnesium sulphate and is concentrated to dryness under reduced pressure (2.7 kPa). The residue is chromatographed on a column of silica gel (0.2-0.063-mm particle size, 4-cm diameter, 50-cm height) and eluted at a pressure of 0.7 bars of nitrogen with a mixture of cyclohexane and ethyl acetate (80-20 by volume), 125-cc fractions being collected. Fractions 3 to 9 are combined and concentrated to dryness under reduced pressure (2.7 kPa) to give 1-(4-chlorobutyl)-5,6-dihydro-(1H,4H)-1,2,5-thiadiazolo[4,3,2-ij]quinoline 2,2-dioxide (4.5 g).

EXAMPLE 7

A solution of 6H-dibenzo[c,e]-1,2-thiazine 5,5-dioxide (5.6 g) in dry N,N-dimethylformamide (10 cc) is added dropwise to a suspension of sodium hydride (0.72 g, 80% suspension in oil) in N,N-dimethylformamide (40 cc). After 30 minutes' stirring, a solution of 1-(3-chloropropyl)-4-phenyl-1,2,3,6-tetrahydropyridine (5.6 g) in N,N-dimethylformamide (20 cc) is added. The reaction mixture is heated to 100° C. for 30 minutes and to reflux for 30 minutes and is then cooled and poured into a mixture of water (300 cc) and ethyl acetate (300 cc). The organic phase is washed with water, is dried over magnesium sulphate and is concentrated to dryness under reduced pressure (2.7 kPa). The residue is chromatographed on a column of silica gel (0.2-0.063-mm particle size, 4-cm diameter, 50-cm height) and eluted with dichloromethane and then a mixture of dichloromethane and ethanol (98-2 and 96-4 by volume), 250-cc fractions being collected. Fractions 8 to 12 are combined and concentrated to dryness under reduced pressure (2.7 kPa). The residue is dissolved in boiling ethanol (200 cc). The hot solution is filtered and treated with a solution of oxalic acid (2 g) in ethanol (20 cc). After cooling, the crystals are filtered off, washed with ethanol and dried. 6-[3-(4-Phenyl-1,2,3,6-tetrahydro-1-pyridyl)propyl]-6H-dibenzo[c,e]-1,2-thiazine 5,5-dioxide hydrogen oxalate (7 g) is obtained, melting at 170° C. (dec.).

6H-Dibenzo[c,e]-1,2-thiazine 5,5-dioxide can be prepared according to the method described by F. Ullmann and C. Grob, Chem. Ber., 43, 2694 (1910).

EXAMPLE 8

A solution of 6H-dibenzo[c,e]-1,2-thiazine 5,5-dioxide (1.7 g) in dry N,N-dimethylformamide (15 cc) is added dropwise to a suspension of sodium hydride (0.25 g, 80% suspension in oil) in N,N-dimethylformamide (5 cc). After 30 minutes' stirring, a solution of 1-(3-chloropropyl)-4-(4-fluorobenzoyl)piperidine (2.1 g) in N,N-dimethylformamide (15 cc) is added. The reaction mixture is heated to 100° C. for 40 minutes and is then cooled and poured into a mixture of water (150 cc) and ethyl acetate (150 cc). The organic phase is washed with water (3×50 cc), is dried over magnesium sulphate and is concentrated to dryness under reduced pressure (2.7 kPa). The residue is chromatographed on a column of silica gel (0.06–0.2-mm particle size, 2-cm diameter, 25-cm height) and eluted with a mixture of cyclohexane and ethyl acetate (50—50 by volume), 30-cc fractions being collected; fractions 7 to 16 are combined and concentrated to dryness under reduced pressure (2.7 kPa). The residue is recrystallized from ethanol (40 cc); the crystals obtained are filtered off, washed with ethanol (5 cc) and dried. 6-[3-(4-(4-fluorobenzoyl)-1-piperidyl)propyl]-6H-dibenzo[c,e]-1,2-thiazine 5,5-dioxide (1.8 g) is obtained, melting at 114° C.

1-(3-Chloropropyl)-4-(4-fluorobenzoyl)piperidine can be prepared as follows: a solution of 1-bromo-3-chloropropane (3.9 cc) and of 4-(4-fluorobenzoyl)piperidine (2.4 g) in acetonitrile (20 cc) is stirred at 25° C. for 20 hours with potassium carbonate (8 g). The mixture is filtered and then concentrated to dryness under reduced pressure (2.7 kPa). The residue is chromatographed on a column of silica gel (0.06–0.2-mm particle size, 2-cm diameter, 20-cm height) and eluted with a mixture of dichloromethane and ethyl acetate (60-40 by volume), 15-cc fractions being collected. Fractions 9 to 17 are combined and concentrated to dryness under reduced pressure (2.7 kPa). 1-(3-Chloropropyl)-4-(4-fluorobenzoyl)piperidine (2.1 g) is obtained in the form of oil.

4-(4-Fluorobenzoyl)piperidine can be prepared according to the method described by R. L. Duncan et al., in J. Med. Chem., 13, 1 (1970).

EXAMPLE 9

A solution of 6H-dibenzo[c,e]-1,2-thiazine 5,5-dioxide (2 g) in dry N,N-dimethylformamide (15 cc) is added dropwise to a suspension of sodium hydride (0.27 g, 80% suspension in oil) in N,N-dimethylformamide (5 cc). After 30 minutes' stirring, a solution of 1-(3-chloropropyl)-4-(4-fluorophenyl)piperazine (2.2 g) in N,N-dimethylformamide (15 cc) is added. The reaction mixture is heated to 100° C. for 1 hour and 15 minutes and is then cooled and poured into a mixture of water (200 cc) and ethyl acetate (180 cc). The organic phase is washed with water (3×80 cc) is dried over magnesium sulphate and is concentrated to dryness under reduced pressure (2.7 kPa). The residue is recrystallized from acetonitrile (60 cc); the crystals obtained are filtered off, washed with acetonitrile (5 cc) and dried. 6-[3-(4-(4-Fluorophenyl)-1-piperazinyl)propyl]-6H-dibenzo[c,e]-1,2-thiazine 5,5-dioxide (2.8 g) is obtained, melting at 163° C.

EXAMPLE 10

A solution of 1H,3H-naphtho[1,8-cd]-1,2,6-thiadiazine 2,2-dioxide (8.8 g) in dry N,N-dimethylformamide (20 cc) is added dropwise to a suspension of sodium hydride (1.2 g, 80% suspension in oil) in N,N-dimethylformamide (50 cc). After 15 minutes' stirring, a solution of 1-(3-chloropropyl)-4-phenyl-1,2,3,6-tetrahydropyridine (9.36 g) in N,N-dimethylformamide (50 cc) is added. The reaction mixture is heated to 100° C. for 1 hour and is then cooled and poured into a mixture of water (500 cc) and ethyl acetate (300 cc). The organic phase is washed with water, is dried over magnesium sulphate and is concentrated to dryness under reduced pressure (2.7 kPa). The residue is redissolved in N,N-dimethylformamide (40 cc) and the solution is diluted with ethanol (300 cc). The precipitate is filtered off, washed with ethanol and dried and then taken up in a 0.1 N aqueous sodium hydroxide solution (200 cc) in which it partially dissolves. The mixture is filtered. The insoluble material is filtered off, washed with water and dried. After recrystallization from ethyl acetate (60 cc), 1,3-bis[3-(4-phenyl-1,2,3,6-tetrahydro-1-pyridyl)-propyl]-1H,3H-naphtho[1,8-cd]-1,2,6-thiadiazine 2,2-dioxide (2.38 g) is obtained, melting at 140° C. The filtrate obtained above is acidified to pH 4 with 1 N hydrochloric acid. The precipitate is redissolved in N,N-dimethylformamide (30 cc) at 100° C., the hot solution is filtered and is then diluted with ethanol (150 cc). The precipitate is filtered off, washed with ethanol (3×50 cc) and dried. 1-[3-(4-Phenyl-1,2,3,6-tetrahydro-1-pyridyl)propyl]-1H,3H-naphtho[1,8-cd]-1,2,6-thiadiazine 2,2-dioxide (0.95 g) is obtained, melting at 240° C.

3-Methyl-1-[3-(4-phenyl-1,2,3,6-tetrahydro-1-pyridyl)propyl]-1H,3H-naphtho[1,8-cd]-1,2,6-thiadiazine 2,2-dioxide can be prepared as follows: sodium hydride (0.105 g, 80% suspension in oil) is added to a solution of 1-[3-(4-phenyl-1,2,3,6-tetrahydro-1-pyridyl)-propyl]-1H,3H-naphtho[1,8-cd]-1,2,6-thiadiazine 2,2-dioxide (0.66 g) in dry N,N-dimethylformamide (20 cc). After 15 minutes' stirring, methyl iodide (3 cc) is added. The reaction mixture is stirred at 20° C. for 1 hour and is then diluted in a mixture of water (200 cc) and ethyl acetate (200 cc). The organic phase is washed with water, is dried over magnesium sulphate and is concentrated to dryness under reduced pressure (2.7 kPa). After chromatography on a column of silica gel (0.2-0.063-mm particle size, 2-cm diameter, 40-cm height) and elution with mixtures of cyclohexane and ethyl acetate (50—50, then 25-75 by volume) and then with pure ethyl acetate, the isolated product is recrystallized from ethyl acetate (20 cc). 3-Methyl-1-[3-(4-phenyl-1,2,3,6-tetrahydro-1-pyridyl)propyl]-1H,3H-naphtho[1,8-cd]-1,2,6-thiadiazine 2,2-dioxide (0.15 g) is obtained, melting at 146° C.

1H,3H-Naphtho[1,8-cd]-1,2,6-thiadiazine 2,2-dioxide can be prepared according to the method described by C. W. Rees et al., J. Chem. Soc., 993 (1971).

EXAMPLE 11

A solution of 2,3-dihydronaphtho[1,2-d]-3-isothiazolone 1,1-dioxide (1.7 g) in dry N,N-dimethylformamide (20 cc) is added dropwise to a suspension of sodium hydride (0.27 g, 80% suspension in oil) in N,N-dimethylformamide (30 cc). After 30 minutes' stirring, a solution of 1-(3-chloropropyl)-4-phenyl-1,2,3,6-tetrahydropyridine (1.94 g) in N,N-dimethylformamide (10 cc) is added. The reaction mixture is heated to 80° C. for 90 minutes and is then cooled and poured into a mixture of water (200 cc) and ethyl acetate (200 cc). The organic phase is washed with water, is dried over magnesium sulphate and is concentrated to dryness under reduced pressure (2.7 kPa). The residue is chromatographed on a column of silica gel (0.2-0.063-mm particle size, 3-cm diameter, 40-cm height) and eluted with a mixture of cyclohexane and ethyl acetate (50—50 by volume), 60-cc fractions being collected. Fractions 5 to 12 are combined and concentrated to dryness under reduced pressure (2.7 kPa). After recrystallization from ethyl acetate 2-[3-(4-phenyl-1,2,3,6-tetrahydro-1-pyridyl)-propyl]-2,3-dihydronaphtho[1,2-d]-3-isothiazolone 1,1-dioxide (1.7 g) is obtained, melting at 150° C.

2,3-Dihydronaphtho[1,2-d]-3-isothiazolone 1,1-dioxide is prepared according to the method described by H. P. Kaufmann et al., Ber. 6, 1499 (1922).

EXAMPLE 12

A solution of (3RS)-3-phenyl-1,2-benzisothiazole 1,1-dioxide (3 g) in dry N,N-dimethylformamide (15 cc) is added dropwise to a suspension of sodium hydride (0.37 g, 80% suspension in oil) in N,N-dimethylformamide (10 cc). After 30 minutes' stirring, a solution of 1-(3-chloropropyl)-4-(4-fluorophenyl)piperazine (3.2 g) in N,N-dimethylformamide (10 cc) is added. The reaction mixture is heated to 100° C. for 1 hour and is then cooled and treated with a mixture of water (200 cc) and dichloromethane (100 cc). The organic phase is washed with water (2×80 cc), is dried over magnesium sulphate and is concentrated to dryness under reduced pressure (2.7 kPa). The residue is chromatographed on a column of silica gel (0.06-0.2-mm particle size, 3-cm diameter, 35-cm height) and eluted with a mixture of cyclohexane and ethyl acetate (60-40 by volume), 30-cc fractions being collected. Fractions 13 to 24 are combined and concentrated to dryness under reduced pressure (2.7 kPa). The residue is dissolved in boiling ethanol (20 cc) and the hot solution is then treated with a solution of fumaric acid (0.8 g) in water (15 cc). The crystals obtained are filtered off, washed with ethanol (5 cc) and with ether (10 cc) and are dried. (3RS)-2-[3-(4-(4-Fluorophenyl)-1-piperazinyl)propyl]-3-phenyl-1,2-benzisothiazole 1,1-dioxide sesquifumarate (2.6 g) is obtained, melting at 182° C.

3-Phenyl-1,2-benzisothiazole 1,1-dioxide can be prepared as follows: N-tert-Butyl-2-(α-hydroxybenzyl)benzenesulphonamide (10 g) is added to a solution of concentrated sulphuric acid (80 cc) cooled to 0° C. The mixture is then stirred at 25° C. for 1 hour and then poured into iced water (800 cc). After 1 hour's stirring, the precipitate is filtered off and is then taken up with dichloromethane (100 cc). The organic solution is washed with water (2×50 cc), is dried over magnesium sulphate and is concentrated to dryness under reduced pressure (2.7 kPa). 3-Phenyl-1,2-benzisothiazole 1,1-dioxide (7.1 g) is obtained, melting at 118° C.

N-tert-Butyl-2-(α-hydroxybenzyl)benzenesulphonamide can be prepared a follows: a 1.6 M solution of N-butyllithium in hexane (64 cc) is added to a solution of N-tert-butylbenzenesulphonamide (8.5 g) in dry tetrahydrofuran (100 cc), cooled to 0° C. After 1 hour's stirring, a solution of benzaldehyde (6.5 cc) in dry tetrahydrofuran (30 cc) is added and stirring at 0° C. is then continued for 2 hours. The mixture is treated with 2 N hydrochloric acid (30 cc) and is extracted with ethyl acetate (100 cc); the organic solution is washed with water (50 cc), is dried over magnesium sulphate and is concentrated to dryness under reduced pressure (2.7 kPa). The solid residue is washed with isopropyl ether (50 cc), and is filtered off and dried. N-tert-Butyl-2-(α-hydroxybenzyl)benzenesulphonamide (11.7 g) is obtained, melting at 160° C.

N-tert-Butylbenzenesulphonamide can be prepared by the method described by J. G. Lombardino, J. Org. Chem., 36, 1843, (1971).

EXAMPLE 13

A solution of (3RS)-3-phenyl-1,2-benzisothiazole 1,1-dioxide (2.45 g) in dry N,N-dimethylformamide (10 cc) is added dropwise to a suspension of sodium hydride (0.3 g, 80% suspension in oil) in N,N-dimethylformamide (5 cc). After 30 minutes' stirring, a solution of 1-(3-chloropropyl)-4-phenylpiperidine (2.4 g) in N,N-dimethylformamide (5 cc) is added. The reaction mixture is heated to 100° C. for 1 hour and 30 minutes and is then cooled and concentrated to dryness under reduced pressure (0.1 kPa). The residue is chromatographed on a column of silica gel (0.06–0.2-mm particle size, 3-cm diameter, 30-cm height) and eluted with a mixture of cyclohexane and ethyl acetate (50—50 by volume), 50-cc fractions being collected. Fractions 12 to 24 ar combined and concentrated to dryness under reduced pressure (2.7 kPa). The residue is dissolved in boiling ethanol (10 cc) and the hot solution is treated with a solution of fumaric acid (0.37 g) in water (5 cc). The crystals obtained are filtered off, washed with ethanol (5 cc), and with ether (10 cc) and are dried. (3RS)-3-Phenyl-2[-3(4-phenyl-1-piperidyl)propyl]-1,2-benzisothiazole 1,1-dioxide hydrogen fumarate (1.6 g) is obtained, melting at 191° C.

1-(3-Chloropropyl)-4-phenylpiperidine can be obtained as follows: a solution of 4-phenylpiperidine (8 g) and of 1-bromo-3-chloropropane (20 cc) in acetonitrile (80 cc) is stirred at 25° C. for 24 hours with potassium carbonate (28 g). The mixture is filtered and is then concentrated to dryness under reduced pressure (2.7 kPa). The residue is chromatographed on a column of silica gel (0.06–0.2-mm particle size, 3-cm diameter, 25-cm height) and eluted with a mixture of cyclohexane and ethyl acetate (50—50 by volume), 60-cc fractions being collected. Fractions 6 to 10 are combined and concentrated to dryness under reduced pressure (2.7 kPa). 1-(3-Chloropropyl)-4-phenylpiperidine (8 g) is obtained in the form of oil.

EXAMPLE 14

A solution of N-(1-naphthyl)methanesulphonamide (6.6 g) in dry N,N-dimethylformamide (20 cc) is added dropwise to a suspension of sodium hydride (0.9 g, 80% suspension in oil) in N,N-dimethylformamide (50 cc). After stirring for 15 minutes, a solution of 1-(3-chloropropyl)-4-(4-fluorophenyl)piperazine (7.2 g) in N,N-dimethylformamide (20 cc) is added. The reaction mixture is heated to 110° C. for 2 hours and 30 minutes and is then cooled and poured in a mixture of water (300 cc) and ethyl acetate (500 cc). The organic phase is washed with water, is diluted with dichloromethane (50 cc), is dried over magnesium sulphate and is concentrated to dryness under reduced pressure (2.7 kPa) down to 50 cc. The crystals are filtered off and washed with ethyl acetate (3×50 cc) and then with isopropyl ether (2×30 cc) and are dried. After recrystallization, from ethyl acetate (300 cc), N[3-(4-(4-fluorophenyl)-1-piperazinyl)propyl]-N-(1-naphthyl)methanesulphonamide (4.84 g) is obtained, melting at 170° C.

EXAMPLE 15

A solution of N-(1-naphthyl)methanesulphonamide (6.6 g) in dry N,N-dimethylformamide (10 cc) is added dropwise to a suspension of sodium hydride (0.9 g, 80% suspension in oil) in N,N-dimethylformamide (50 cc). After 30 minutes' stirring, a solution of 1-(3-chloropropyl)-4-phenyl-1,2,3,6-tetra-hydropyridine (7.2 g) in N,N-dimethylformamide (20 cc) is added. The reaction mixture is heated to reflux for 1 hour and is then cooled and poured into a mixture of water (300 cc) and ethyl acetate (300 cc). The organic phase is washed with water, is dried over magnesium sulphate and is concentrated to dryness under reduced pressure (2.7 kPa). The residue is chromatographed on a column of silica gel (0.2-0.063-mm particle size, 4-cm diameter, 60-cm height) and eluted with dichloromethane and then with a mixture of dichloromethane and ethanol (98-2 and 96-4 by volume), 250-cc fractions being collected. Fractions 11 to 15 are combined and concentrated to dryness under reduced pressure (2.7 kPa). After recrystallization from ethyl acetate (80 cc), N-[3-(4-phenyl-1,2,3,6-tetrahydro-1-pyridyl)propyl]-N-(1-naphthyl)methanesulphonamide) (4.57 g) is obtained, melting at 162° C.

EXAMPLE 16

A solution of N-phenylbenzenesulphonamide (2.34 g) in dry N,N-dimethylformamide (10 cc) is added dropwise to a suspension of sodium hydride (0.24 g, 80% suspension in oil) in N,N-dimethylformamide (50 cc). After 15 minutes' stirring, a solution of 1-(3-chloropropyl)-4-phenyl-1,2,3,6-tetrahydropyridine (2.34 g) in N,N-dimethylformamide (20 cc) is added. The reaction mixture is heated to 140° C. for 1 hour and then cooled and poured into a mixture of water (200 cc) and ethyl acetate (200 cc). The organic phase is washed with water, is dried over magnesium sulphate and is concentrated to dryness under reduced pressure (2.7 kPa). The residue is chromatographed on a column of silica gel (0.2-0.063-mm particle size, 4-cm diameter, 40-cm height) and eluted with dichloromethane and with a mixture of dichloromethane and ethanol (98-2 and 96-4 by volume), fractions 250-cc being collected. Fractions 5 to 9 are combined and concentrated to dryness under reduced pressure (2.7 kPa). After recrystallization from isopropyl ether (150 cc), N-[3-(4-phenyl-1,2,3,6-tetrahydropyridyl)propyl]-N-phenylbenzenesulphonamide (2.4 g) is obtained, melting at 112° C.

EXAMPLE 17

A solution of benzo[c,d]-2-indolone (4.5 g) in dimethylformamide (25 cc) is run over 30 minutes into a mixture of sodium hydride (1.3 g as a 50% dispersion in liquid paraffin) and of dimethylformamide (10 cc) under a stream of argon. The reaction mixture is stirred at 100° C. for 30 minutes and is then cooled to a temperature close to 20° C. 1-(3-Bromopropyl)-4-phenyl-1,2,3,6-tetrahydropyridine (9.3 g) in dimethylformamide (20 cc) is then added over 10 minutes. The reaction mixture is stirred under reflux for 2 hours and is then cooled to a temperature close to 20° C. The residual oil is concentrated to dryness at 40° C. under reduced pressure (20 mm Hg; 2.7 kPa) and is then purified by flash chromatography on a silica column, under a stream of argon, at a moderate pressure (0.5-1.5 bars) with ethyl acetate as eluent. N-[3-(4-Phenyl-1,2,3,6-tetrahydropyridyl)-propyl]benzo[c,d]-2-indolone (7.4 g) is obtained in the form of a yellow oil (hydrogen oxalate; melting point: 138° C).

1-(3-Bromopropyl)-4-phenyl-1,2,3,6-tetrahydropyridine can be prepared as follows: phosphorus tribromide (2.7 cc) is run into 1-(3-hydroxypropyl)-4-phenyl-1,2,3,6-tetrahydropyridine (8.7 g) in toluene (100 cc). The mixture is heated to reflux for 2 hours and is then cooled to a temperature close to 20° C. The precipitate formed is filtered off on sintered glass and is then taken up with dichloromethane (250 cc) and distilled water (150 cc). The organic phase is separated off, dried over anhydrous magnesium sulphate and is filtered and concentrated to dryness at 40° C. under reduced pressure (20 mm Hg; 2.7 kPa). 1-(3-Bromo-propyl)-4-phenyl-1,2,3,6-tetrahydropyridine (14 g) is obtained in the form of hydrobromide salt (melting point: 185° C.), employed in the crude state in the subsequent syntheses.

1-(3-Hydroxypropyl)-4-phenyl-1,2,3,6-tetrahydropyridine can be prepared as follows: 3-bromopropanol (25 cc), triethylamine (73.4 cc) and 4-phenyl-1,2,3,6-tetrahydropyridine hydrochloride (51.5 g) in toluene (700 cc) are heated to boiling for 16 hours. The mixture is then cooled to a temperature close to 20° C. and is then concentrated to dryness at 40° C. under reduced pressure (20 mm Hg; 2.7 kPa). 1-(3-Hydroxypropyl)-4-phenyl-1,2,3,6-tetrahydropyridine (42 g) is obtained in the form of a dark oil which crystallises (melting point <40° C.), employed in the crude state in the subsequent syntheses.

The medications according to the invention consist of a compound of formula (I) in free form or in the form of an addition salt with a pharmaceutically acceptable acid, in the pure state or in the form of a composition in which it is coupled with any other pharmaceutically compatible product, which may be inert or physiologically active. The medications according to the invention can be employed orally, parenterally, rectally or topically.

Tablets, pills, powders (gelatin capsules, cachets) or granules can be employed as solid compositions for oral administration. In these compositions, the active substance according to the invention is mixed with one or more inert diluents such as starch, cellulose, sucrose, lactose or silica, under a stream of argon. These compositions may also comprise substances other than diluents, for example one or more lubricants such as magnesium stearate or talc, a colorant, a coating (coated tablets) or a varnish.

Pharmaceutically acceptable solutions, suspensions, emulsions, syrups and elixirs containing inert diluents such as water, ethanol, glycerol, vegetable oils or liquid paraffin may be employed as liquid compositions for oral administration. These compositions may include substances other than diluents, for example wetting products, sweeteners, thickeners, flavors or stabilizers.

Sterile compositions for parenteral administration may be preferably aqueous or nonaqueous solutions, suspensions or emulsions. Water, propylene glycol, a polyethylene glycol, vegetable oils, especially olive oil, injectable organic esters, for example ethyl oleate, or other suitable organic solvents may be employed as a solvent or carrier. These compositions may also contain adjuvants, especially wetting agents, agents producing isotonicity, emulsifiers, dispersants and stabilizers. The sterilization can be performed in various ways, for example by asepticizing filtration, by incorporating sterilizing agents in the composition, by irradiation or by heating. They can also be prepared in the form of sterile solid compositions which may be dissolved in sterile water or any other injectable sterile medium at the time of use.

The compositions for rectal administration are suppositories or rectal capsules which, in addition to the active product, contain excipients such as cocoa butter, semisynthetic glycerides or polyethylene glycols.

The compositions for topical administration may be, for example, creams, pomades, lotions, eye lotions, mouth washes, nose drops or aerosols.

In human therapeutics the compounds according to the invention are particularly useful for the treatment of disorders involving serotonin and especially disorders of the central nervous system, of the cardiovascular system and intestinal disturbances. In particular, they are useful for the treatment of anxiety, of sleep disturbances, of depression, of psychoses and especially of schizophrenia, of migraine, of asthma, of high pressure and of urticaria, as analgesics and as inhibitors of platelet aggregation.

The doses depend on the effect which is sought after, on the duration of the treatment and on the route of administration which is employed; they are generally between 10 and 300 mg daily orally in the case of an adult with unit doses ranging from 5 to 150 mg of active substance.

In general the practitioner will determine the appropriate dosage as a function of the age, weight and all the other factors pertaining to the individual to be treated.

The following examples illustrate compositions according to the invention:

EXAMPLE A

Gelatin capsules containing 50 mg of active substance having the following composition are prepared by the usual technique:

| | |
|---|---|
| 1-[3-(4-phenyl-1,2,3,6-tetrahydro-1-pyridyl)propyl]-5,6-dihydro(1H,4H)-1,2,5-thiadiazolo[4,3,2-ij-quinoline 2,2-dioxide | 50 mg |
| cellulose | 18 mg |
| lactose | 55 mg |
| colloidal silica | 1 mg |
| sodium carboxymethyl starch | 10 mg |
| talc | 10 mg |
| magnesiums stearate | 1 mg |

EXAMPLE B

Tablets containing 50-mg doses of active product having the usual composition are prepared according to the usual technique:

| | |
|---|---|
| 1,3-bis[3-(4-phenyl-1,2,3,6-tetrahydro- | 50 mg |

-continued

| | |
|---|---|
| 1-pyridyl)propyl]-1H,3H-naphtho[1,8-cd]-1,2,6-thiadiazine 2,2-dioxide | |
| lactose | 104 mg |
| cellulose | 40 mg |
| polyvidone | 10 mg |
| sodium carboxymethyl starch | 22 mg |
| talc | 10 mg |
| magnesium stearate | 2 mg |
| colloidal silica | 2 mg |
| mixture of hydroxymethyl cellulose, glycerine, titanium oxide (71-3.5-24.5) q.s. | 1 coated tablet finished at 245 mg |

EXAMPLE C

An injectable solution containing 10 mg of active product having the following composition is prepared:

| | |
|---|---|
| 1-[3-(4-(4-fluorophenyl)piperazinyl)propyl]-5,6-dihydro(1H,4H)-1,2,5-thiadiazolo-[4,3,2-ij]quinoline | 10 mg |
| benzoic acid | 80 mg |
| benzyl alcohol | 0.06 cc |
| sodium benzoate | 80 mg |
| 95% ethanol | 0.4 cc |
| sodium hydroxide | 24 mg |
| propylene glycol | 1.6 cc |
| water q.s. | 4 cc |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. A compound of the formula:

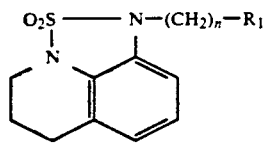

in which
R₁ denotes
a 1,2,3,6-tetrahydro-1-pyridyl radical substituted in the 4- position by (a) a phenyl radical, (b) a phenyl radical substituted by a halogen atom or an alkyl, hydroxyl or alkoxy radical, (c) a 3-indolyl radical, (d) a 3-indolyl radical substituted on the nitrogen atom by an alkyl or alkylcarbonyl radical and/or in the 5- position by a chlorine or fluorine atom or (e) a 3-(5-hydroxyindolyl) radical,
a 1-piperazinyl radical substituted in the 4-position by (a) a phenyl radical, (b) a phenyl radical substituted by an alkoxy, alkyl, hydroxyl, nitro or amino radical or a halogen atom, (c) a 1,2-benzisothiazol-3-yl radical, (d) a 1,2-benzisoxazol-3-yl radical or (e) a 2-pyridyl radical, a piperidino radical substituted in the 4- position by (a) a phenyl radical, (b) a phenyl radical substituted by a halogen atom or a hydroxyl, alkyl or alkoxy radical, (c) two phenyl radicals, (d) a bis(4-fluorophenyl)methylene radical, (e) a 4-fluorobenzoyl radical, (f) a 2-oxo-1-benzimidazolinyl radical, (g) a 2-oxo-1-benzimidazolinyl radical substituted in the 3-position by an alkylcarbonyl or benzoyl radical, (h) a hydroxyl radical and a phenyl radical optionally substituted by an alkyl, alkoxy or hydroxyl radical or a halogen atom, (i) a 3-indolyl radical, (j) a 3-indolyl radical substituted on the nitrogen atom by an alkyl or alkylcarbonyl radical and/or in the 5-position by a chlorine or fluorine atom or (k) a 3-(5-hydroxyindolyl) radical,
n is equal to 2, 3 or 4,
and their salts with inorganic or organic acids, it being understood that the alkyl and alkoxy radicals or the alkyl parts contain from 1 to 4 carbon atoms as a straight or branched chain.

2. The compound of formula (I) according to claim 1, in which R₁ denotes a 4-phenyl-1,2,3,6-tetrahydro-1-pyridyl, 4-phenylpiperidino, 4-(4-fluorobenzoyl)piperidyl or 4-phenyl-1-piperazinyl radical whose phenyl nucleus is optionally substituted by a halogen atom or a hydroxyl radical.

3. A pharmaceutical composition for treating a disease ameliorated by serotonin antagonists which comprises a compound according to claim 1 or an addition salt thereof with a pharmaceutically acceptable acid, in association with a pharmaceutically acceptable carrier.

4. A pharmaceutical composition for treating a disease ameliorated by serotonin antagonists which comprises a compound according to claim 2 or an addition salt thereof with a pharmaceutically acceptable acid, in association with a pharmaceutically acceptable carrier.

5. A method of treating a disease ameliorated by serotonin antagonists which comprises administering to a subject capable or benefiting from such treatment an effective amount of a compound of formula (I) as defined in claim 1 or of a pharmaceutically acceptable salt thereof.

* * * * *